United States Patent [19]
Whittaker

[11] Patent Number: 5,934,046
[45] Date of Patent: Aug. 10, 1999

[54] INDIVIDUAL DENTAL FLOSS PACKAGE FORMING METHOD AND APPARATUS

[76] Inventor: Dale Whittaker, 7506 S. 93rd East Ave., Tulsa, Okla. 74133

[21] Appl. No.: 09/080,907

[22] Filed: May 18, 1998

Related U.S. Application Data

[63] Continuation-in-part of application No. 08/732,692, Oct. 18, 1996, Pat. No. 5,765,343
[60] Provisional application No. 60/005,752, Oct. 20, 1995, abandoned.

[51] Int. Cl.$^6$ ..................................................... B65B 63/04
[52] U.S. Cl. ................................ 53/430; 53/116; 53/450; 53/553; 53/555; 242/533.4; 242/538
[58] Field of Search .............................. 53/116, 118, 430, 53/450, 553, 555, 591; 242/DIG. 3, 440, 531, 538, 548, 533.4, 533.5

[56] References Cited

U.S. PATENT DOCUMENTS

| | | |
|---|---|---|
| D. 312,710 | 12/1990 | Whittaker . |
| D. 334,249 | 3/1993 | Whittaker . |
| 2,782,809 | 2/1957 | Smallridge . |
| 2,861,601 | 11/1958 | Marzolf . |
| 2,889,610 | 6/1959 | Buddecke . |
| 3,541,756 | 11/1970 | Mateski . |
| 3,975,883 | 8/1976 | Besnyo et al. . |
| 4,255,917 | 3/1981 | Stone . |
| 4,408,726 | 10/1983 | Leonov et al. . |
| 4,746,075 | 5/1988 | Hoxit . |
| 4,972,946 | 11/1990 | Whittaker . |
| 5,121,584 | 6/1992 | Suter . |
| 5,209,042 | 5/1993 | Rickard . |

*Primary Examiner*—Daniel B. Moon

[57] ABSTRACT

There is disclosed apparatus and method for packaging individual strand segments of a strand material, such as dental floss, including apparatus for carrying out a method of supplying strand material to a rotatable strand positioning element through a hollow shaft thereof positioned to wind the strand material around a selected mandrel of a circular array of mandrels together with controlling the moving of mandrels within and removing mandrels from within the circular path of the rotating strand positioning element and for counting the rotations of the strand positioning element and using that rotation count to control the advance of the array of mandrels wherein the mandrels having openings for entry of a pick-off element and are caused to be lowered to leave the coil of strand material on the pick-off element, following which the coil of strand material is urged forward by an air jet to be captured between two sheets of packaging film and transported to a stage where the packaging film sheets are sealed together around the coil to form a package in a chain of packages which then may be separated to form individual packages.

10 Claims, 11 Drawing Sheets

INDIVIDUAL DENTAL FLOSS PACKAGE FORMING METHOD AND APPARATUS

CROSS-REFERENCE TO RELATED APPLICATIONS

This application is a continuation-in-part of my application Ser. No. 08/732,692, filed Oct. 18, 1996 now U.S. Pat. No. 5,765,343, which claims priority from provisional application Serial No. 60/005,752 filed Oct. 20, 1995 now abandoned.

BACKGROUND OF THE INVENTION

The present invention relates to methods and apparatus for producing a small individual package containing a single strand of filamentary materia such as dental floss or the like coiled within about a four square inch area and having a number of turns sufficient to provide a strand of at least about eighteen inches in length.

The packaging of dental floss and other filamentary material has tended to utilize a spool or some variation thereof to wind a substantial quantity of the filamentary material, typically 50 feet or more, leaving it to the ultimate user to cut off a length of the filamentary material suitable for the intended purpose. It has been recognized that in certain applications of filamentary materials, such as dental floss, it would be convenient to provide an individual package, sealed against contamination, containing a pre-cut length of the filamentary material suitable for the intended purpose. For products such as dental floss, for example, any such packaging must be produced in a very economical manner in order that it not vastly exceed the value of the product being packaged.

An example of forms of individual dental floss packaging is shown in Whittaker U.S. Pat. No. 4,972,946, issued Nov. 27, 1990 (U.S. Cl. 206/210); to a lesser extent the state of the art with respect to such packaging is exemplified in the references cited in the foregoing patent. Typical efforts at providing individual packaging for dental floss or other filamentary material involved winding a length of the filamentary material on a spindle formed of a flat piece of plastic or paperboard before placing it in the package or placing an unsupported length of filamentary material in the package in some indeterminate manner.

Copending parent application Ser. No. 08/732,692 U.S. Pat. No. 5,765,343 referenced herein is incorporated by reference in this application.

SUMMARY OF THE INVENTION

The packages according to the invention provide a desirable way of packaging and distributing dental floss or other filamentary material for convenience of the ultimate user. Improvements in preserving sterility or avoiding contamination will be apparent as compared with the common method of distribution by a bulk package containing a spool, reel or magazine of dental floss. Also, the individual packaging according to the invention provides the possibility of supplying the dental floss coated with solid and liquid materials, and the package can also be modified to include other dental hygiene products. If desired, the package may be formed to be opened by separating down the middle to release the coil of dental floss while the two halves of the package remain attached to the ends of the dental floss and aid in the manipulation thereof.

Particular novelty resides in the rapid and efficient apparatus and method for creating coils of dental floss (which may be somewhat square sided) in a serial fashion and then placing each of them in an individual package formed around the coil.

While sealed plastic film packages containing relatively short lengths of filamentary material are not new in and of themselves, some previous filament packages employ a spindle on which the filament is wound, while others insert the filament in a random, disordered manner. The present invention provides a highly efficient and effective method and means for forming coils of material in a serial arrangement and for incorporating each of such coils in an individually sealed plastic package with improved forms of electromechanical apparatus to carry out the packaging method.

BRIEF DESCRIPTION OF THE DRAWINGS

In addition to providing the advantages and fulfilling the objects described above, other advantages and features of the invention will be apparent from the following description in conjunction with the appended drawings in which:

FIG. 18 is a plan view of the apparatus of FIG. 17;

DETAILED DESCRIPTION OF THE PREFERRED EMBODIMENTS

Figure 1:
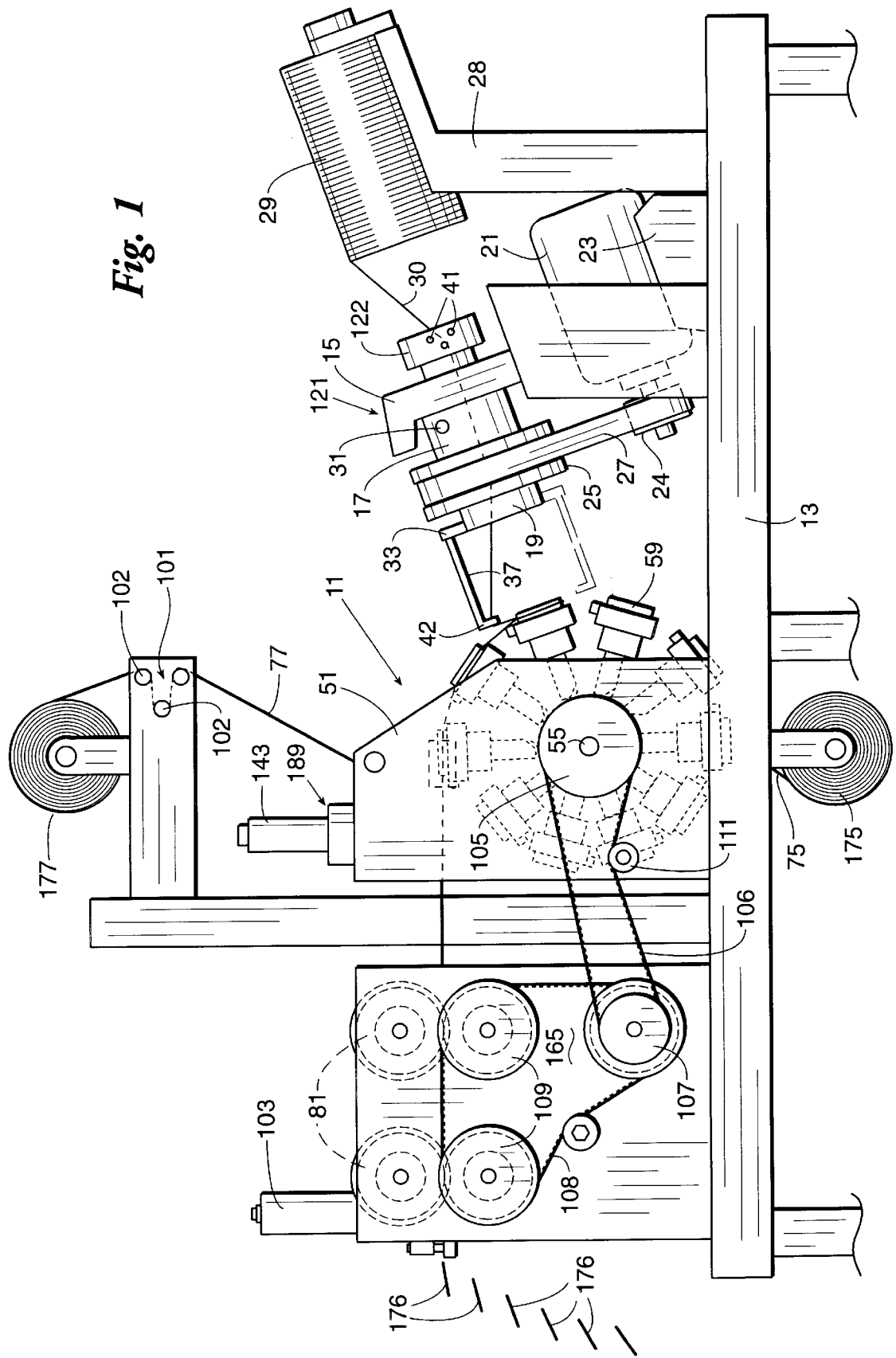
FIG. 1 shows a partially schematic side elevational fragmentary view of apparatus useful in carrying out the invention.

Referring now to the drawings, and particularly FIG. 1 through FIG. 4B, apparatus 11 exemplifies package forming machinery useful and well adapted for carrying out the invention to produce individual sealed packages of coiled filamentary material such as dental floss.

Apparatus such as that shown may be employed to carry out the process according to the invention in a highly automated manner so that all of the steps of sub-processes and of the complete process will be performed rapidly and in the proper sequence. It is desired to perform some or all of the following steps in an automated manner with little or no manual intervention by a machine operator. The necessary or desired steps are: 1) supplying a strand material to a rotating strand positioning element or winder element, 2) causing a first of a series of mandrels to reside within a path of rotation of the strand positioning element, 3) rotating the strand positioning element, preferably at several rotations per second to wind turns of strand on the first mandrel, 4) moving the first mandrel out of the path of the rotating strand positioning element of the winder and replacing it with a second mandrel of the series of mandrels, 5) removing the coiled strand portion wound on the first mandrel, preferably retaining its coiled shape, at the same time that the winder element is winding strand on a subsequent mandrel, 6) repeating steps 1 through 5 substituting the second mandrel for the first mandrel and substituting a third mandrel for the second mandrel and so on to produce a series of connected coils of strand material, 7) feeding the series of coils separated by about one diameter and connected seriatim by lengths of the strand material between two elongated sheets of plastic film material, 8) sealing together the two elongated sheets of flexible plastic material in a manner to enclose each of the coils in a separate individual container, and 9) severing the individual packages one from the other and simultaneously severing the strand of filamentary material joining the coils.

As shown in FIGS. 1 through 4, the packaging apparatus 11 according to the invention is provided with a base 13 on which is mounted support element 15 by which a rotatable cylinder 17 is mounted in bearings (not shown).

A winding disc 19 is fixedly mounted on cylinder 17 to rotate with cylinder 17 which is driven by motor 21 in motor mounting 23 through sprockets 24 and 25 and sprocket belt 27. Retainer 28 accepts a dental floss supply roll 29 which may or may not be rotatably fixed relative to retainer 28.

A timing disc 31 mounted on cylinder 17 allows a magnetic, photoelectric or electromagnetic sensor (not shown) to read the position and velocity of winding disc 19. A cantilever arm 33 is mounted on winding disc 19 for rotation therewith. Cantilever arm 33 carries a winder element 37 while disc 19 is provided with a suitable counterweight (not shown) to provide balance and minimize vibration due to the rapidly rotating structure associated with winding disc 19. This apparatus may be designated the strand positioning element.

As winding disc 19 and the associated mechanism rotates, the dental floss supply roll 29 feeds floss 30 from roll 29 through tension guides 41 and through winding point 42. As dental floss 30 is drawn off the end of element 37 at winding point 42, dental floss is fed from the end of supply roll 29 which thereby does not need to be rotating. The supply roll 29 may be altered or replaced to provide a rotating roll which may be positioned with its axis transverse to the axis of winding disc 19, or any other known form of strand supply may be employed. Tension guides 41 are adapted to control a drag on floss 30 from supply roll 29. The floss 30 is preferably fed in a zig-zag path around two or more of the tension guides 41 in the form of hard metal pins. By increasing or decreasing the degree of wrap on the guides the friction drag can be set to provide the desired tension in the floss 30 passing through winding point 42. Other known tension control means could be substituted for tension guides 41.

Floss strand 30 enters winder drive assembly 121 through a hollow shaft 122 and proceeds to the end of the winder element 37 where it passes through an eye in winding point 42. The eye (not shown) may take the form of a cylinder of glass or other hard material with an opening of one-eighth to one-quarter inch. The eye is preferably removable and replaceable as it will be subject to abrasive wear even though formed of a hard material.

The apparatus thus described serves to wind turns of dental floss 30 around mandrels 59 mounted on wheel 57. Floss strand 30 is wound around a mandrel 59 a predetermined number of turns selected for this example to be five turns. The diameter of mandrels about which the floss strand 30 is wound is approximately one inch and five or six turns of floss strand will provide a floss length in the finished package of from 15 to 20 inches which is the generally desired value.

Each rotation of disc 19 and, hence, of winder element 37 is sensed by conventional means such as a magnetic reed switch responsive to a magnet fixed on disc 19 or similarly arranged optical sensing devices employed to create one or more pulse signals for each rotation of disc 19 and winder element 37. Such pulse signals are counted by a suitable electromechanical or solid state counter in the monitor and control panel and utilized to control certain functions of the packaging system. In the systems illustrated by way of example, a pulse generated shortly after winder element 37 passes its top position (e.g. 10° to 60°) causes initiation of the operation of stepper motor 53 to rotate the mandrel assembly by 36°. The speed of operation of stepper motor 53 in rotating the mandrel assembly is sufficiently fast relative to the rotational speed of winder element 37 so that the mandrel 59 having just been wound with five turns and the mandrel 59 which takes its place both pass winder element 37 before it reaches the lower part of its circular path where it would interfere with the arriving mandrel 59. By way of example, a rotational velocity of 400 RPM for winder element 37 is compatible with a stepping motor time amounting to approximately 50 msecs (for 36° of rotation of the mandrel assembly). In other terms, one might state that rotation of the winder element of as much as 90° to 120° during the transition from one mandrel to another is acceptable without causing interference between the winder and the movement of the mandrels.

An alternative control mode may provide faster rotation of the winder element 37 without interference with the mandrels in motion. In this mode, the speed of the winder would be set to and maintained at approximately one revolution during the mandrel transition time produced by the stepping motor. The rotation of the winder should, in any case, be between 270° and 480° during the mandrel transition time. Generally, for this higher rotation speed mode, the position of the winder at the start of the mandrel transition would also be somewhat past (30° to 180°) the top of the winder path. In this mode, winder element 37 crosses the mandrel's motion path before the arrival of the next mandrel and then precedes it so that interference is avoided.

It should be understood that there are numerous well known forms of winding mechanisms which could be employed in whole or in part in place of the winding mechanism (strand positioning element) of FIG. 1 shown associated with winding disc 19. For example, the arm 33 could hesitate or reduce velocity when completing a coil to all the mandrel to be shifted. Therefore, the method and apparatus of the invention should not be considered to be limited to the form of winding mechanism shown by way of illustration in FIG. 1.

Figure 2:
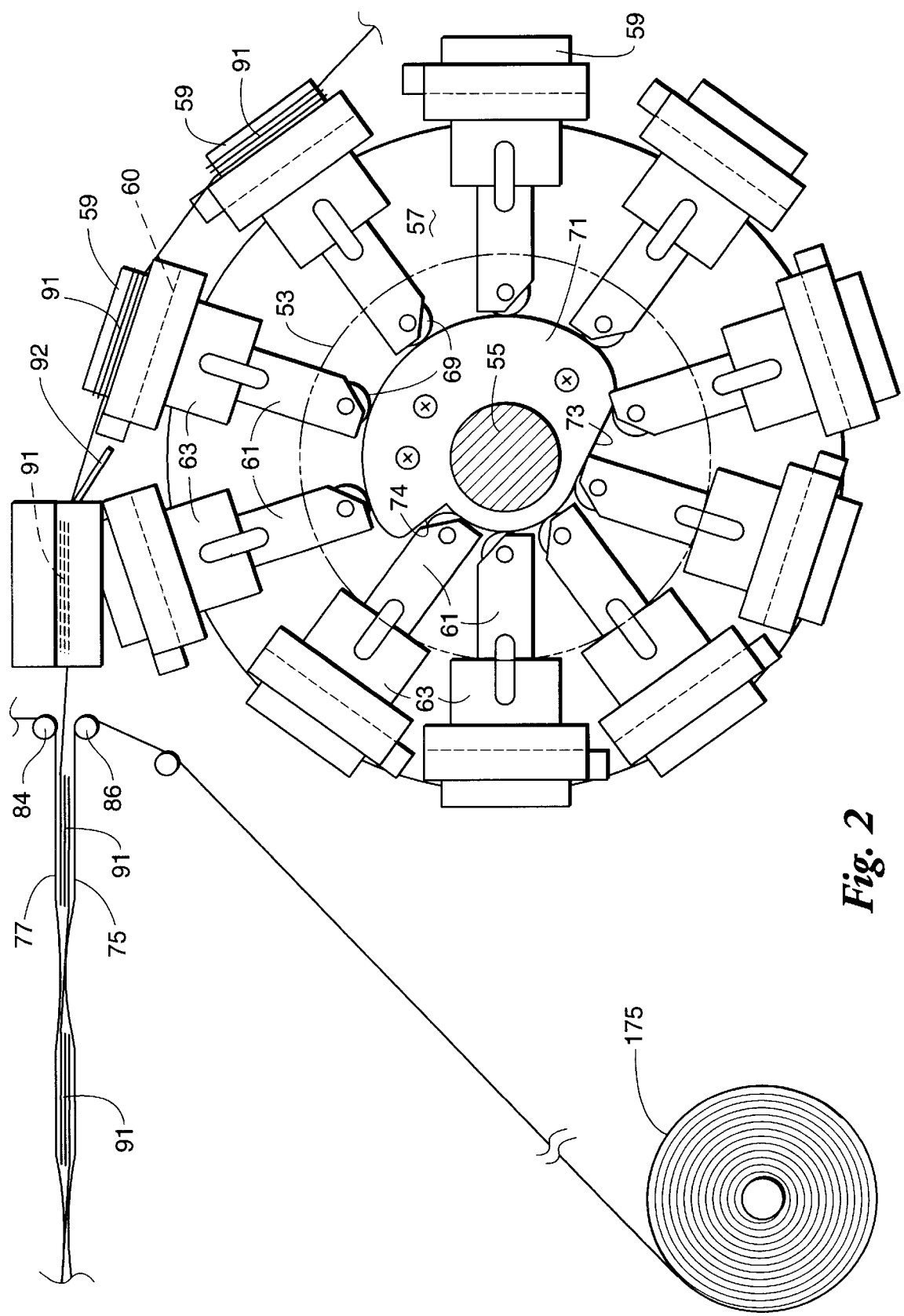
FIG. 2 shows an enlarged detailed fragmentary view of a portion of the apparatus not fully shown in FIG. 1.
Figure 3:
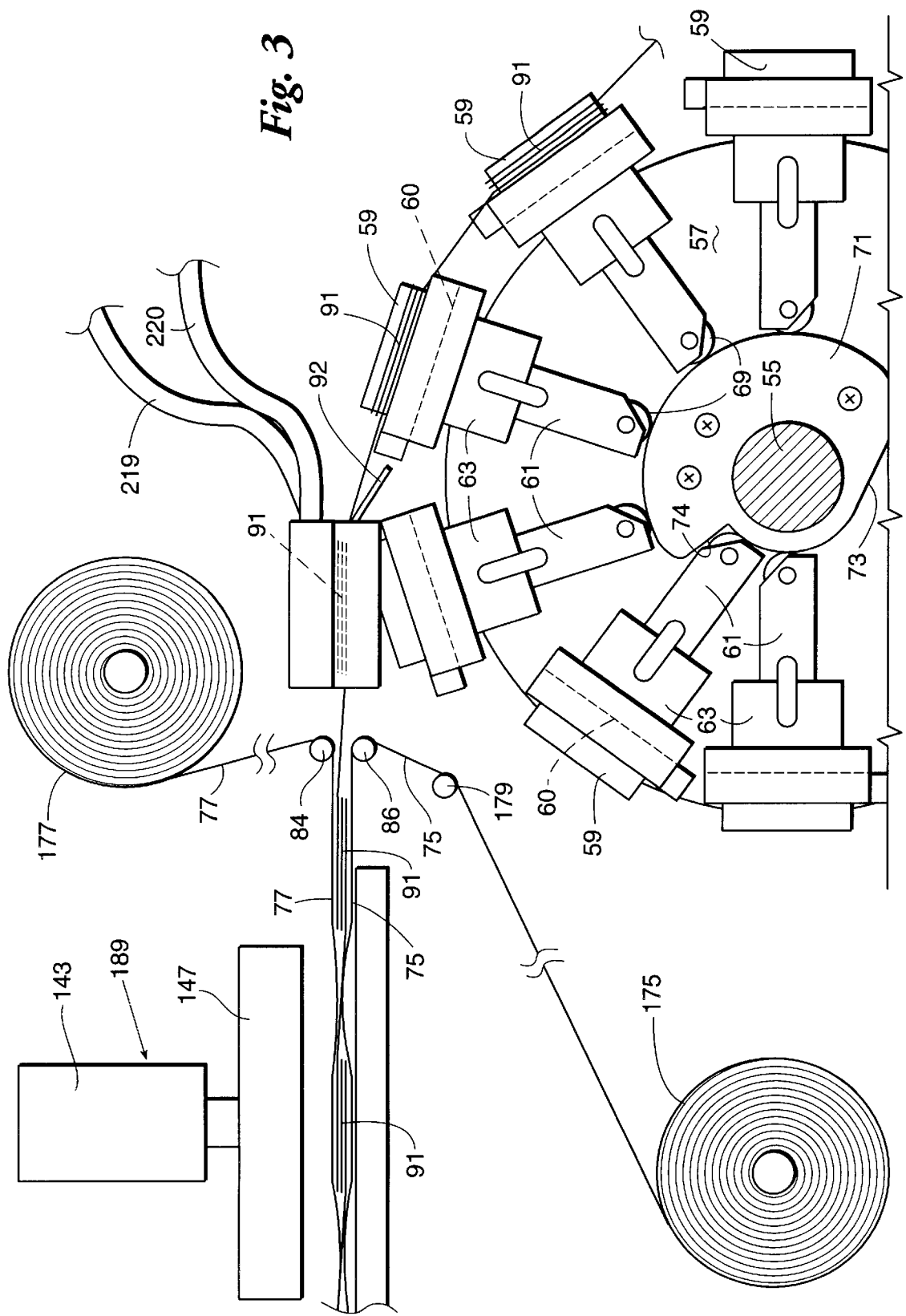
FIG. 3 shows details including heat sealing elements of apparatus as shown in FIG. 1.

Referring now to FIGS. 2 and 3 as well as to FIG. 1, a frame 51 (preferably secured to and supported on base 13) supports a motor 53 having a shaft 55 on which is mounted wheel 57 carrying mandrels 59. Motor 53 is preferably a stepping motor capable of rapidly rotating wheel 57 through a predetermined fraction of a rotation; in the example shown the predetermined stepwise rotation is 36° or 1/10th of a rotation. Step wise motion of wheel 57 alternatively may be achieved by a pneumatic stepper, a mechanical stepping device, or any combination of the above.

Also mounted on frame 51 in a fixed rather than rotatable manner is cam 71 on which ten (10) cam followers 69 roll and are radially reciprocated by cam 71. Cam 71 extends at least about 90° around the interior of wheel 57 and is provided with a ramp 73 which moves cam followers 69 outward and a sharp dropoff 74 allowing cam followers 69 to move inward at the location of dropoff 74.

Cam followers 69 are connected to respective mandrels 59 by radial rods 61 and slidably mounted in brackets 63. Rods 61 are spring (not shown) operating between rod 6 and bracket 63 which urges each of the mandrels 59 to an inward or retracted position. Clearly, many other forms of specific apparatus could be utilized to provide for sequential extension and retraction of mandrels 59 as well known in the mechanical arts. For example, electric solenoids or fluid pressure actuators could be employed for operating the extension and retraction motion of mandrels 59 and conventional control apparatus could be utilized to actuate such mechanisms at the desired positions of rotation of wheel 57. Preferably mandrels 59 are formed of hard plastic material rather than steel or other metal to thereby reduce the total mass and inertia of wheel 57 and the mandrels mounted thereon. Reduction of mass and inertia bases the power requirement for motor 53 which, in any case, will require one or several horsepower input at periodic peak power intervals.

A conventional control system (not shown) causes the rapid step motion of wheel 57 and mandrels 59 mounted thereon to occur when cantilever arm 33 is rotated approximately 90° from the position shown in FIG. 1 thereby avoiding interference between the step motion of mandrels 59 and the winding point 42 on strut element 37. Any possible such interference may also be avoided by increasing the radius of the circle of motion of winding point 42, by making the mandrels oblong or rectangular in shape rather than circular as shown in drawings and/or allowing element 37 to pivot slightly during its rotational motion. Following the stepwise motion of the mandrel located coaxially with cylinder 17, the winding mechanism associated with winding disc 19 repeats the process of winding a predetermined number of turns on the next mandrel.

Figure 11:
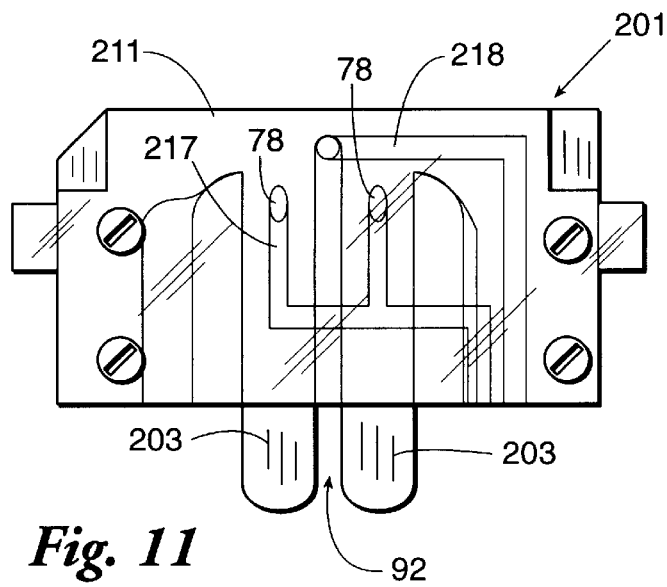
FIG. 11 is a top plan view of the pick-off element cooperating with the apparatus of FIG. 8.
Figure 12:
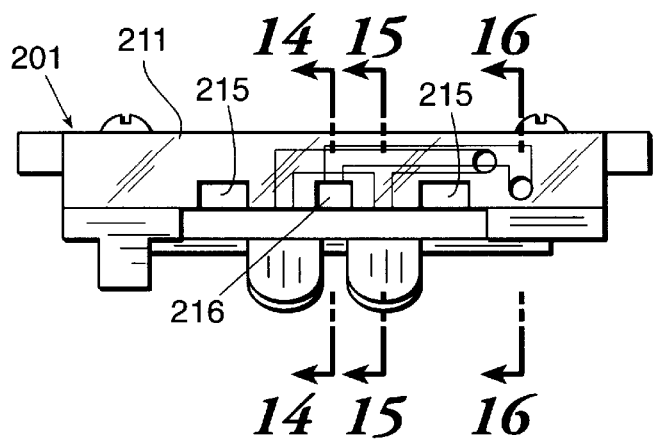
FIG. 12 is a front elevational view of the pick-off element of FIG. 11.
Figure 13:
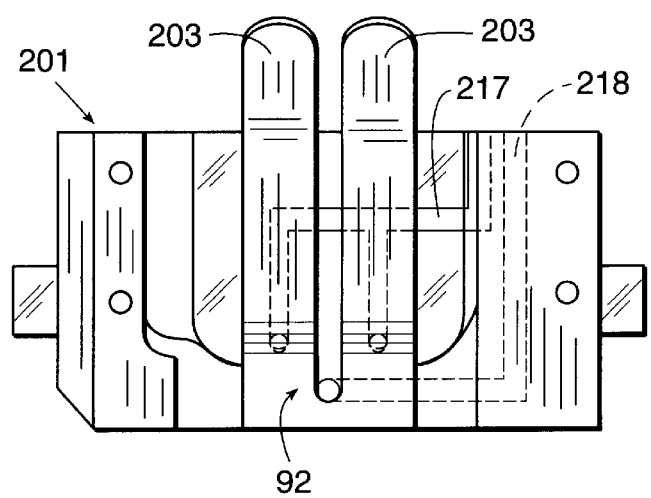
FIG. 13 is a bottom plan view of the pick-off element of FIG. 11.
Figure 14:
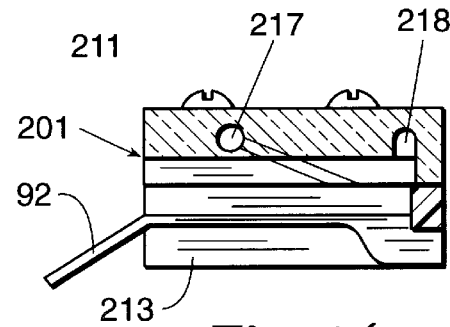
FIG. 14 is a sectional view taken along lines 14—14 in FIG. 12.
Figure 15:
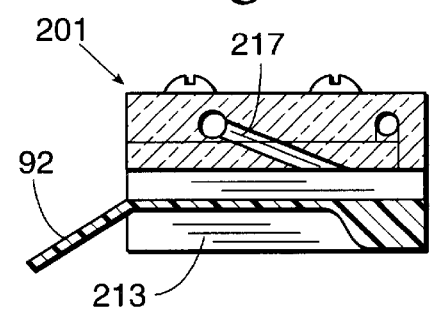
FIG. 15 is a sectional view taken along lines 15—15 in FIG. 12.
Figure 16:
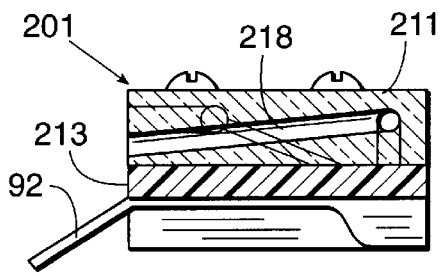
FIG. 16 is a sectional view taken along lines 16—16 in FIG. 12.

As best shown in FIG. 2, a mandrel 59 positioned at or near the top of the wheel will be caused to retract when its cam follower 69 reaches the dropoff 74 of cam 71. Each mandrel 59 is transversed by generally diametrical slots 60 as indicated by dashed lines in FIG. 2 and also in FIGS. 8, 9, and 10. The slots may occupy from a quarter to one-half of the diameter of the mandrel 59 and may have a depth of about one-half inch or less. Slots 60 may be combined in a single central slot, if desired. A pick-off element 90 best shown in FIGS. 11–16 for receiving coils 91 of dental floss 30 has a tongue 92 shaped and dimensioned to fit within slots 60 thereby lifting coils 91 from mandrels 59 when they are retracted. A gentle air stream provided by air jets from openings 78 (see FIG. 11, for example) moves coil 91 forward to be captured by an upper plastic film 77 from supply roll 177 and a lower plastic film 75 from supply roll 175 between rolls 84 and 86. Further rollers such as 81 and 82 (see FIG. 4A) transport the sandwiched interconnected dental floss coils to be sealed into rectangular enclosures by a package sealing apparatus shown schematically as heat sealer press 89 and platen 99 (in FIG. 3).

Preferably rolls 81, 82, 84 and/or 86 are operated cyclically in synchronism with the stepping of wheel 57 and mandrels 59. The distance of travel of film 77 and film 75 in each step cycle preferably is no greater than the peripheral travel of wheel 57 and mandrels 59, and it may be slightly less to allow for relaxation of tension in floss 30.

Figure 4A:
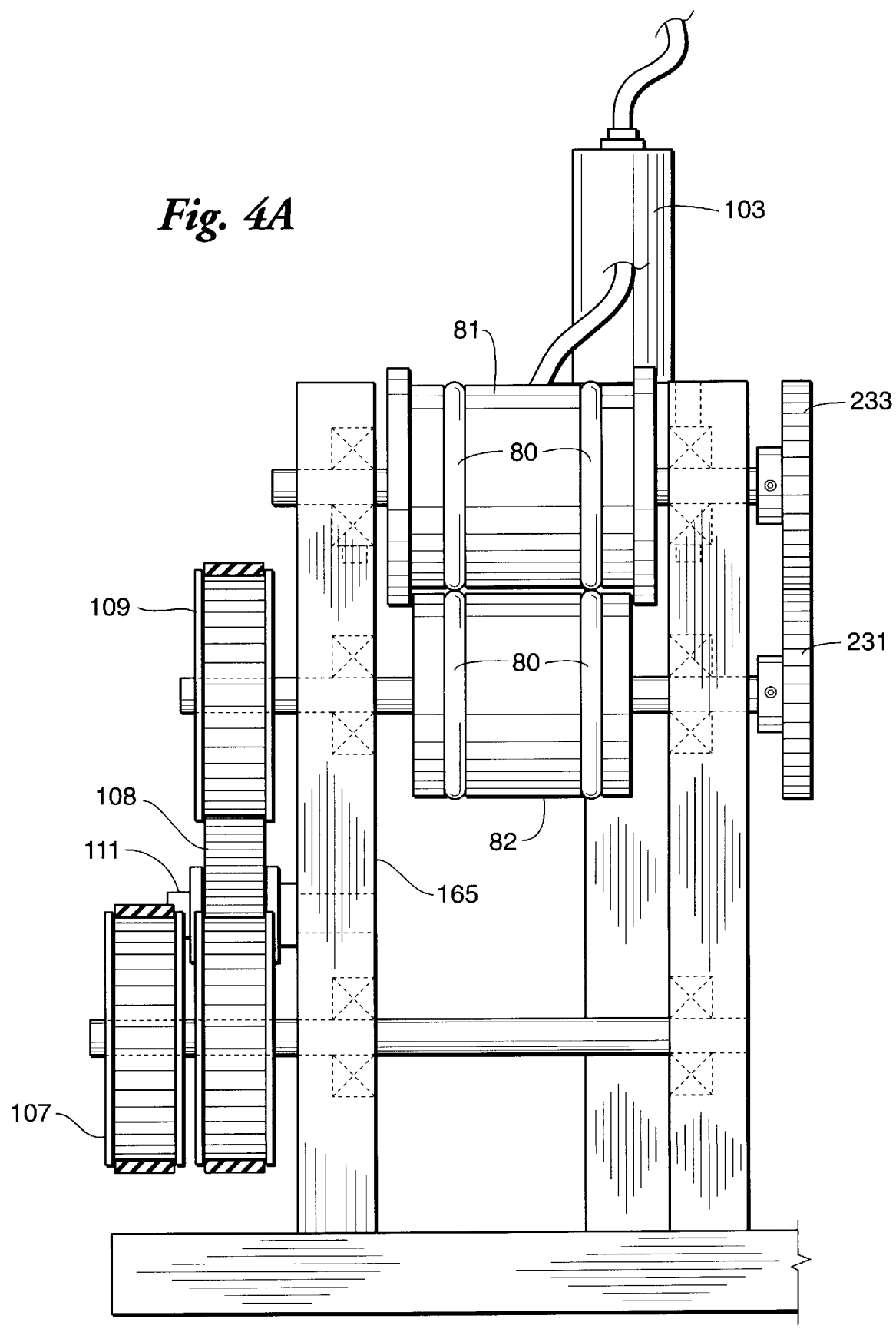
FIGS. 4A and 4B show details of apparatus useful in placing and sealing coils of filamentary material in flexible plastic individual packages.
Figure 4B:
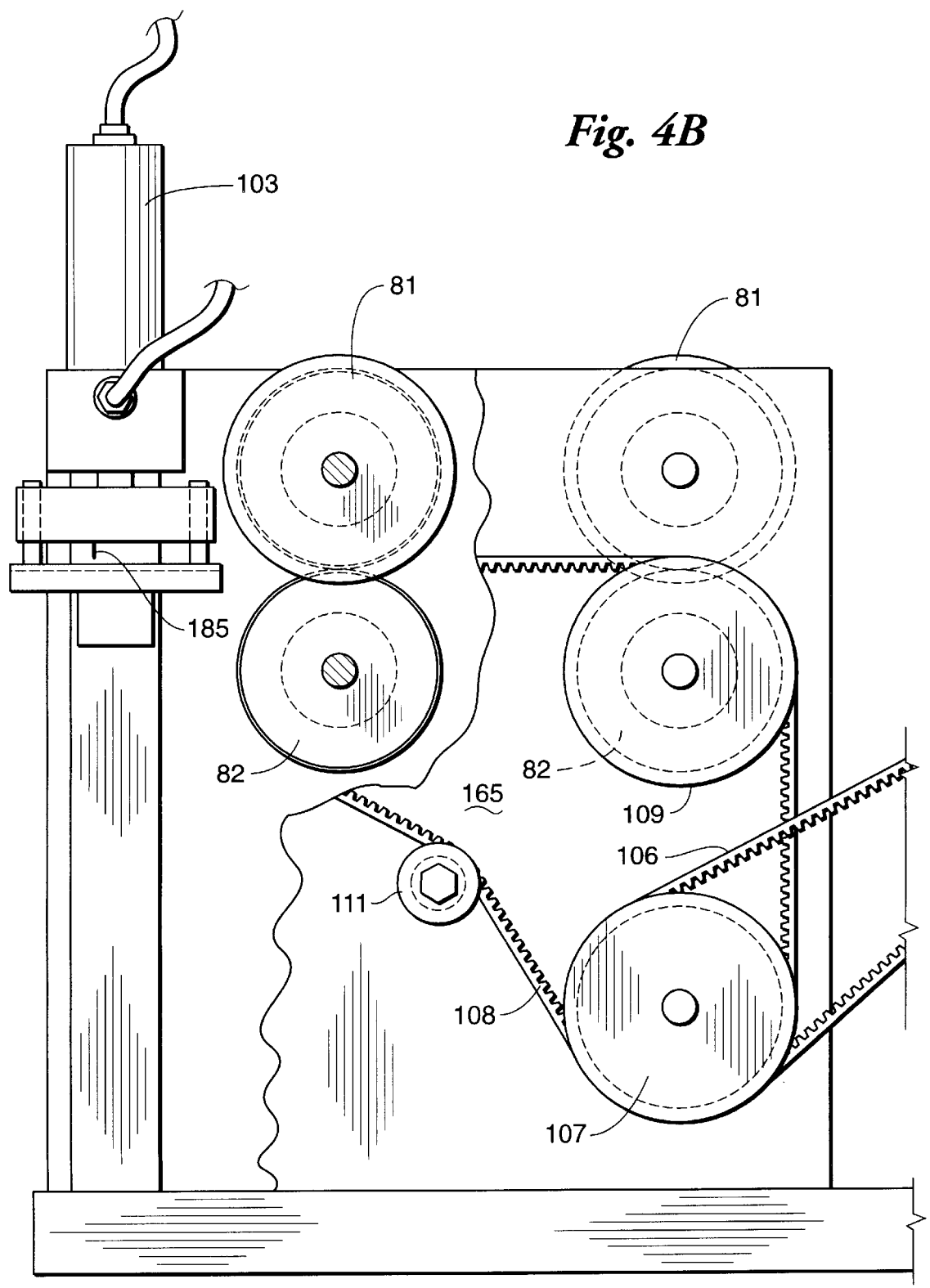

FIG. 3 shows heat seal press 189 which operates to make one or more sealed enclosures surrounding a coil of dental floss in each operation of the press. The completed packages which have not yet been severed into individual units may be fed onto any suitable conveyor. The packages can be severed into individual units 176 as shown in FIG. 1 immediately following the heat sealing step by a conventional cutter blade 191 as shown in FIG. 4B or may be transported to a separate station for any desired further processing, such as imprinting, sterilizing, or the like, and lastly being severed into individual packages.

Alternatively the films 77 and or 75 may be preprinted with product information and the film feed may employ a photo sensor for sensing registration marks and independently control the film feed in response thereto.

Other forms of apparatus than that shown in FIGS. 1, 2, 3, and 11-16 may be employed to cleanly separate the coils from the retracting mandrels and convey it to be sandwiched between film 77 and 75 and sealed into packages by press 89. For example, a belt may be provided which encircles wheel 57 and is provided with openings mating with the bifurcated top portion of mandrels 59. The belt may have a periphery greater than that of wheel 57 and be provided with one or more idler pulleys so that it departs from the surface of wheel 57 at the point where the mandrels are retracted. This generally horizontal position of the belt would then serve to support the coils where they are overlaid by a top film sheet and then, at a point where they leave the belt, they sandwich between the upper film 77 and a lower film 75. Such a belt arrangement could cooperate with or substitute for tongue 92 in providing clean separation of the dental floss coils from the mandrels and from the surface of the wheel 57.

Various optional features are shown in FIGS. 1–4; for example, a tension control 101 may be provided for upper film 77 in the form of staggered pins 102 or cylinders presenting frictional resistance to the passage of film 77. A similar tension control may be provided for film 75. Other conventional forms of tension control could be substituted therefor including passive and active forms as well as adjustable or non-adjustable tension control apparatus.

One form of drive mechanism for the rolls 81 and 82 is shown, particularly in FIGS. 1 and 4b. In this embodiment the stepper motor 53 which drives shaft 55 to turn mandrels 59 is coupled through toothed belts and sprockets to drive rolls 81 and 82. A sprocket 105 on shaft 55 drives a smaller sprocket of double sprocket 107 through toothed belt 106. Toothed belt 106 is of conventional form, sometimes referred to as a timing belt, and is provided with teeth which engage sprocket 105 so that there is no slippage in the drive between sprocket 105 and sprocket 107. An idler 111 is provided for maintaining appropriate tension in toothed belt 106.

A larger sprocket of double sprocket 107 similarly engages a toothed belt 108 which drives sprockets 109 thereby driving rolls 82. An idler 111 serves to maintain appropriate tension in toothed belt 108. Preferably, rolls 82 are driven directly and rolls 81 are driven from rolls 82 by means of intermeshing gears 231 and 233 as shown in FIG. 4a.

Preferably, rolls 81 and 82 are provided with plastic, somewhat resilient rings for firmly gripping films 75 and 77 to minimize slippage in feeding the still connected packages through the apparatus. Preferably, rings 80 are spaced apart to be near the edge of packages 93 where they will not encounter the coils 91 of floss or other strand material. Thus the material passing between and engaged by rings 80 will be of uniform thickness to facilitate smooth feeding of the packages. The ratio of the peripheral speed of rolls 81 and 82 and the rings 80 forming a part thereof relative to the peripheral speed of the mandrels 59 on which the floss 30 is wound will be determined by the relative diameters of the various sprockets 105, 107 and 109. It is preferred that the peripheral speed of the interconnected floss windings and that of the film fed through rolls 81 and 82 be approximately equal. It may be found that some floss or other strand material is slightly elongated under the tension of winding and tends to shorten when removed from the mandrels. This could indicate the desirability of a very slightly slower speed (equating to a shorter step distance) for the rolls 81 and 82 as compared with the peripheral speed (step distance) of the mandrels 59. While adjustment of the ratio of speed of rolls 81 and 82 relative to the mandrels 59 may be desirable for maximum uniformity and positioning of the coil windings in the packages, this ratio is not critical and a 1:1 ratio is workable and acceptable in the usual case.

Figure 5:
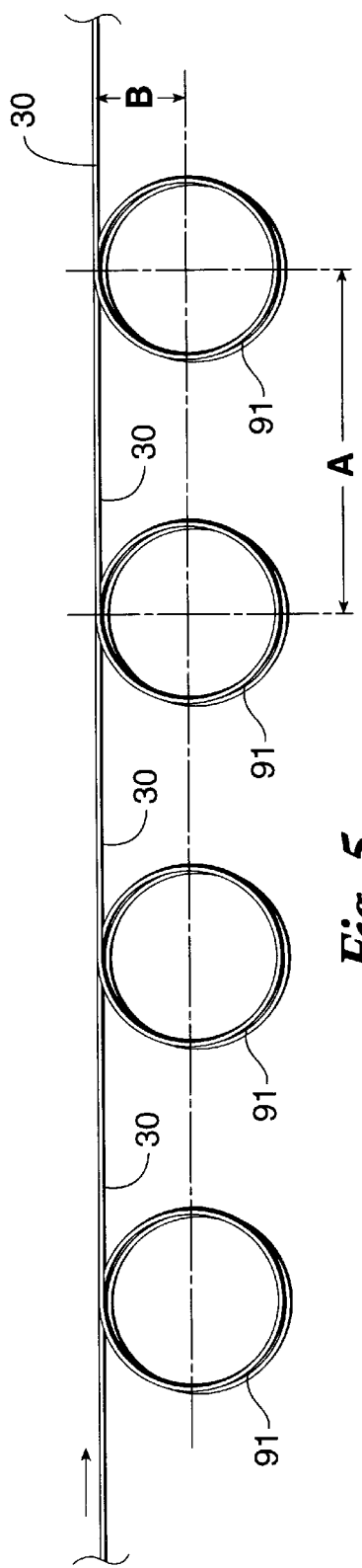
FIG. 5 is a plan view of a series of coils of filamentary material formed according to the invention and useful in explaining the method and apparatus of the invention.
Figure 6:
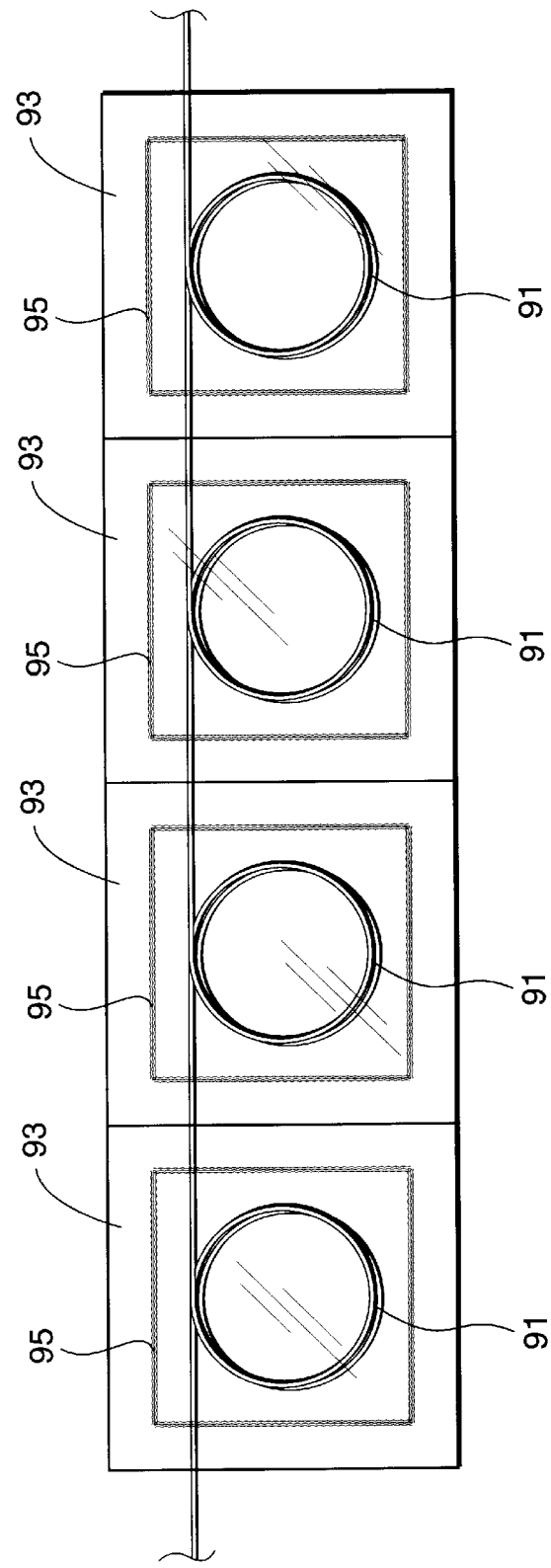
FIG. 6 shows in schematic form one of the last stages of formation of the sealed individual packages of coiled filamentary material.

FIGS. 5 and 6 show an example of the configuration of the coiled dental floss 30 which is formed into coils 91 of radius B; in this example A equals about one half inch and coils 91 have a diameter of about one inch and comprise six turns of floss thereby giving a usable length of dental floss in each package of about eighteen inches. Center to center separation of coils 91 (A in FIG. 5) is about two inches.

FIG. 6 shows the manner in which the square or rectangular seal 95 may be made around the coils 91 to form individual packages 93 and later separate by severing the film strip midway between the coil positions. Packages 93 may be arranged to be opened by tearing in any known or conventional manner and preferably the tear line would run perpendicular to the running filament of floss 30 and midway of the package so that one-half of the torn package would be on each end of the dental floss segment when it was uncoiled.

In an alternative embodiment coils 91 are wound around four posts and, hence, are generally square rather than circular in shape.

Figure 7:
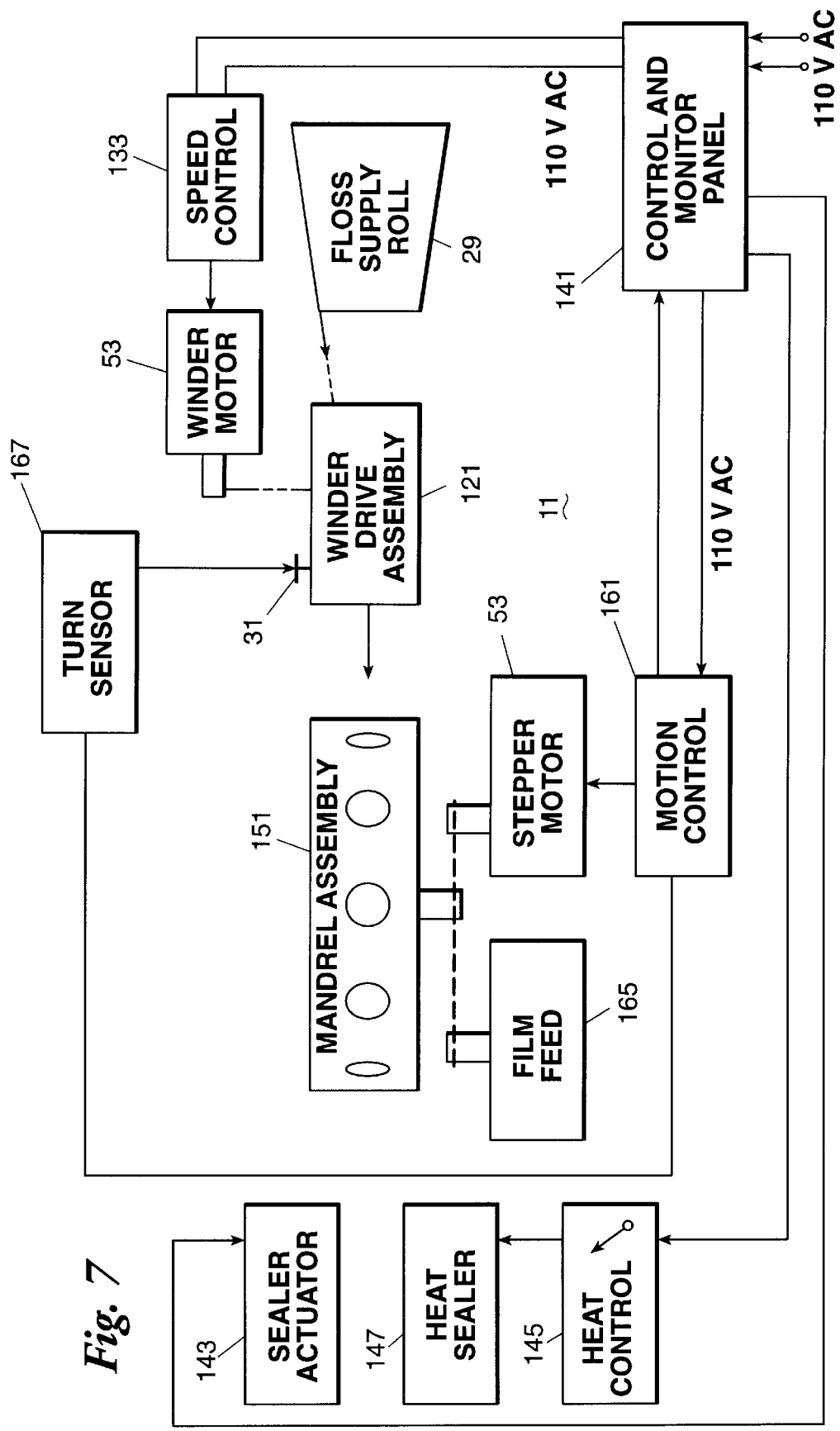
FIG. 7 is a schematic block diagram of an individual dental floss segment packaging system according to the invention.

FIG. 7 shows a schematic block diagram of the principal components of Applicant's system and their relationship together with the basic operating controls for the apparatus. While the diagram in FIG. 7 is particularly related to the preferred embodiment of apparatus illustrated in FIGS. 1 through 4, it is also pertinent to alternative embodiments some of which are mentioned herein.

The packaging apparatus and control system designated 11 includes a winder drive assembly 121 for a rotatable winder element 37 which is supplied with floss 30 from a floss supply roll 29.

Winder drive assembly 121 is driven by a winder motor 21 having a variable speed controllable by a speed control 133. A control and monitor panel 141 supplies power and a control signal to speed control 133.

A mandrel assembly 151 includes rotatably mountable mandrels 59 which are positionable with respect to a winder so that turns of dental floss may be wound thereon. A motor 53 which is preferably a stepper motor is controlled by a motion control 161 which may be responsive to a turn sensor providing a signal indicating the turning of the winder past one or more defined positions in its circular travel. Turn sensor 167 may incorporate a magnetic sensor, an optical sensor, an electromagnetic sensor or other conventional means for sensing the position of the winder.

The control system for the apparatus as illustrated in FIG. 7 may be implemented with electromechanical elements such as relays, motor solenoids, and the like without employing computer control, but the apparatus may also be controlled by appropriately programmed microprocessor computer hardware.

Control and monitor panel 141 also provides power and control signals for a sealer actuator 143 which may take the form of a solenoid operated air valve and cylinder, a heat sealer 147 and a heat control 145 for heat sealer 147. For clarity and simplicity the illustrations do not include conventional apparatus for providing safety features and interlock apparatus for detecting and acting upon depletion of packaging film or of floss strand material, misfeeds, jams and the like. Such apparatus forms no part of the invention and conventional techniques can be employed in respect thereto.

Figures 8, 10:
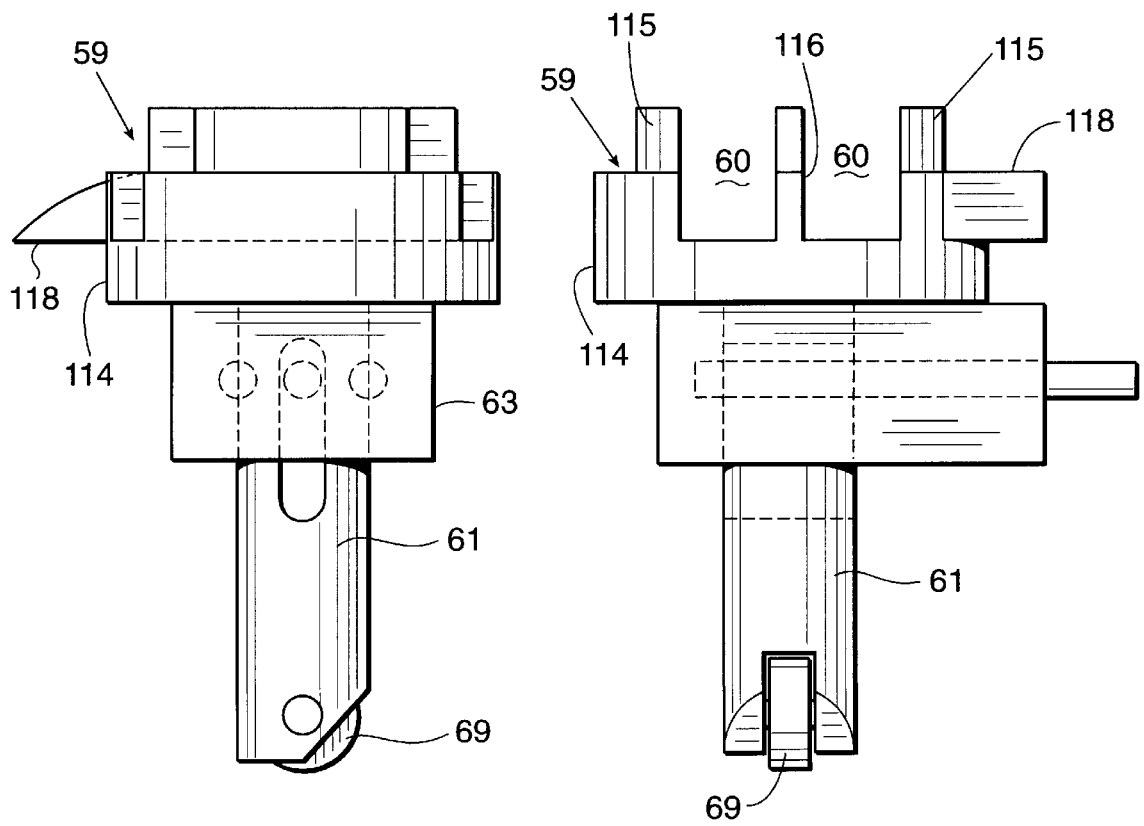
FIG. 8 is a detailed fragmentary side elevational view of a mandrel subassembly from FIG. 1.
FIG. 10 is a detailed front elevational view of the apparatus of FIG. 8.

Referring now to FIGS. 9–16 in addition to FIG. 8, as one of the mandrels 59 approaches the topmost position it encounters pick-off element 90 having a bifurcated or double tongue 92, (see FIG. 13) pick-off element 201 is preferably formed at least in part of a clear plastic material. Each of tongue portions 203 enters mandrel 59 as it approaches the top position in the opening between center wall 116 and outer wall 115 of the mandrel 59, see FIGS. 9 and 10. The ends of tongue portions 203 are bent slightly downward to better conform with the direction of motion of the mandrels 59. Tongue portions 203 insert themselves below the ridge formed at the top of mid-portion 114 of mandrel 59 and hence insert themselves below the floss strand wound on mandrel 59. Floss strand 30 is caused to be wound above mid-portion 114 in part by the action of lip 118 best shown in FIGS. 8, 9 and 10. Lip 118 is provided with a smoothly curved portion at its extremity which intercepts any strand of floss tending to be wound below the top of mid-portion 114 of mandrel 153 and lifts it to the desired position.

Lip 118 also provides a support for the leading segment of a strand of floss running from a trailing mandrel to the mandrel in front of it. This prevents any tendency of the floss strand to sag between mandrels to the extent that it would interfere with operation of the system. It should be pointed out, however, that lip 118 is an optional feature of the mandrel configuration which, in some cases, may not be necessary and may be omitted in whole or in part.

As mandrel 59 approaches the top position it reaches a point where it is no longer maintained at its upper position by cam 71 as the cam follower 69 associated therewith drops to the lower level of cam 71. This action is accelerated by an internal or external spring (as shown at 62 in FIGS 17 and 18, for example) acting on rod 61 drawing the head of mandrel 59 down to a position near its mounting bracket 63. This occurs only shortly after tongue portions 203 have fully penetrated the mandrel 59 so that they support the coil 91 of floss strand 30 being lifted from mandrel 59. A top plate 211 has cutouts 215 which accommodate outer walls 115 of a mandrel and a center cutout 216 which accommodates center wall 116 of a mandrel as it approaches the position where it is about to drop to its lower level. At this point the coil of floss strand is essentially enclosed by tongue portions 203 of pick-off element 201 below the coil and by top plate 211 above the coil while the mandrel is withdrawing itself from within the coil.

While the coil is essentially restrained on all sides, it is, nevertheless, free to move forward upon the initiation of the next mandrel advance cycle and this transitional motion of the coil is caused by an air jet provided through passages 217 and openings 78 in top plate 211.

It will be noted that there is also a separate air passage 218 which is an optional feature of the pick-off element 201. Passage 218 produces a vertical air jet which is present at times when it is desired to prevent a coil 91 or any part of the floss strand 30 which it comprises from moving forward of the designated rest position it should occupy before it is moved forward upon the initiation of the next mandrel advance cycle. This function of restraining the coil in its rest position is well served by the air barrier provided by air passage 218 although it could also be accomplished by use of a sliding pin retracted by a solenoid or other suitable means, if so desired.

As shown in FIG. 3, an air tube 219 provides low pressure air to air passages 217 and air tube 220 provides low pressure air to air passages 218. The flow of air in tubes 219 and 220 and, hence, in passages 217 and 218 is controlled by solenoid air valves associated with control and monitor panel 141 and controlled thereby. As previously described, the purpose of the air jet from passage 218 is to prevent a coil 91 positioned in pick-off element 201 from moving forward prematurely, and it is provided with an air flow to effectuate that purpose until just before air flow is admitted to openings 78 producing a jet or jets which moves the coil forward to be captured between film 75 and film 77. Actuation of air jets from openings 78 may be momentary since little time is required to cause the desired movement of a coil 91 into position between rolls 84 and 86 and films 75 and 77.

Just forward of the exit position for mandrels 59 a lower packaging film strip 75 and an upper packaging film strip 77 are brought together from supply roll 177 and supply roll 175 which are shown only schematically as they would be very large rolls positioned at some distance from the mandrel assembly 151. Conventional tension control apparatus and idler rollers would be arranged in a known manner to provide the film strips at the proper tension in proximity to the exit position for mandrels 59. This apparatus is indicated only schematically by idler rollers 179.

Packaging film strips 75 and 77 are guided to a position of parallelism and close proximity by cylindrical low friction surfaces 84 and 86 or, alternatively, by free-running rolls similarly positioned.

From the description heretofore, it will be appreciated that the apparatus disclosed causes the coil previously wound on a mandrel 59 to be captured between lower packaging film strip 75 and upper packaging film strip 77 and transported to the next stage of the process in which it is operated on by heat sealer 147 actuated by heat sealer actuator 189. In the case of floss coils with a nominal transverse dimension of one inch, it is found convenient to have the traverse of the coils between successive mandrel positions determined at about two inches and the width of the packaging film strip 75 and 77 to also be approximately two inches. With this arrangement, a heat sealer 189 may be designed to produce a substantially square seal between the lower film strip 75 and the upper packaging film strip 77 effectively encapsulating the coil removed from a mandrel 59 while leaving intact the coil strand entering and leaving the capsule. The transverse dimensions of the peripheral heat seal may be from one and one-half to one and three-quarters inches.

After the continuous length of encapsulated coils of floss strand exits the rolls 81 and 82 of the film feed 165, the strip may be wound on a large supply coil for further processing or it may be cut into individual packages approximately two inches by two inches as a part of the same operation.

Figure 17:
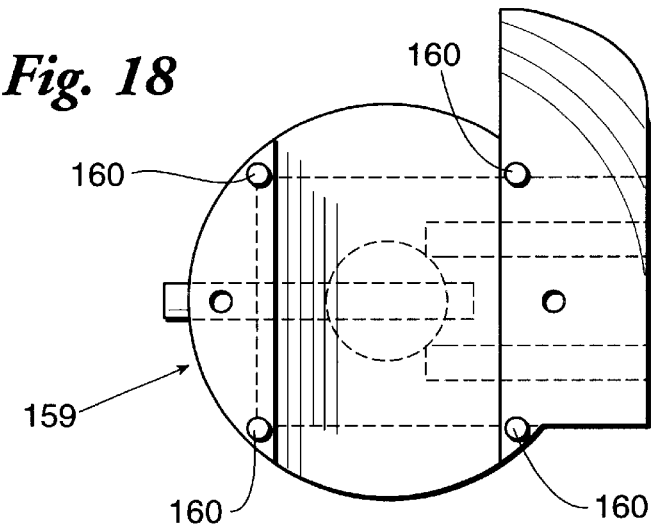
FIG. 17 is a detailed fragmentary side elevational view of an alternative form of mandrel subassembly.
Figure 19:
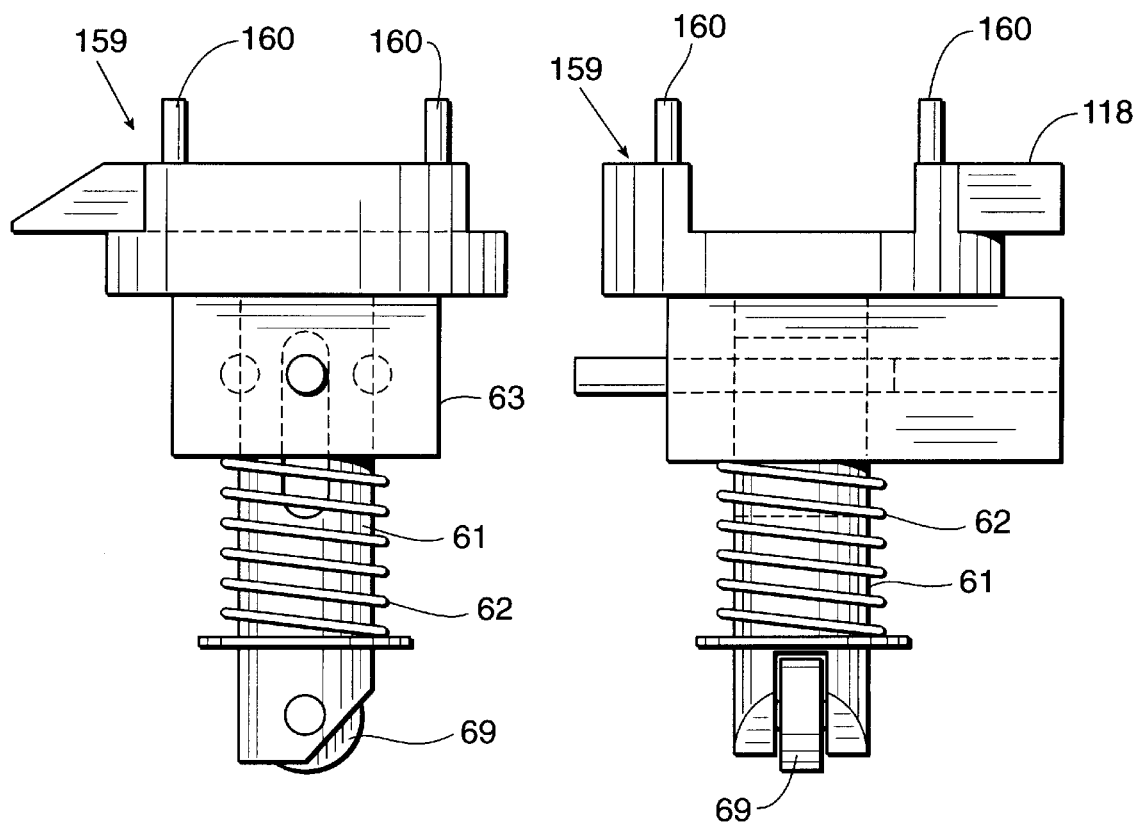
FIG. 19 is a detailed front elevational view of the apparatus of FIG. 17.

FIGS. 17, 18, and 19 show an alternative form of mandrel which is preferred in most dental floss packaging machine operations. The function of mandrels 159 shown in FIGS. 17–19 is very similar to that of mandrels 59 shown in FIGS. 8–10 described heretofore.

Mandrels 159 differ from mandrels 59 in that they are provided with metal pins 160 which serve as the form on which the floss or other strand is wound on the mandrel. In FIGS. 17–19 pins 160 are four in number and arranged in a rectangle or a square.

Accordingly, the floss coil wound on mandrels 159 will have a somewhat rectangular shape rather than being in the form of a circle.

A primary advantage of the metal pins 160 is that they may be made of a hard stainless steel or other hard material which can better resist the abrasive effect of the floss winding operation. Also, even though metal pins 160 are eventually abraded, they may readily be replaced without replacing the entire mandrel 159. Metal pins 160 may be press-fit into openings in the plastic mandrel body, may be threaded and screwed in place, or may be emplaced in any known or conventional manner.

Figure 9:
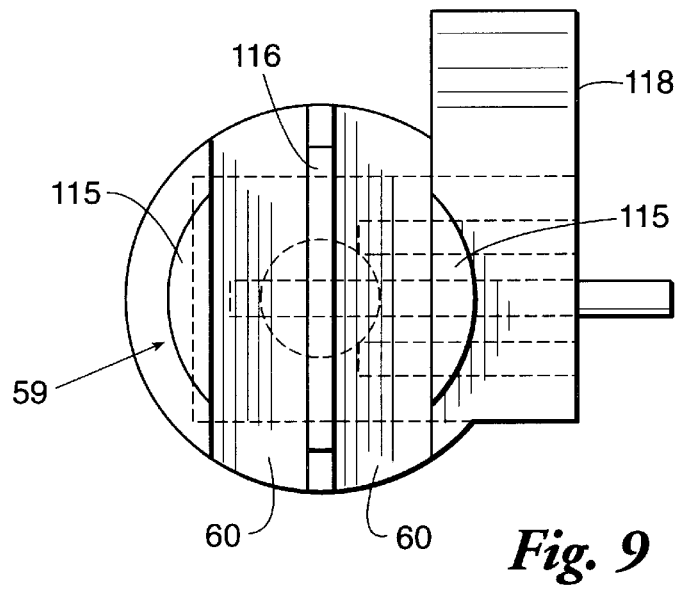
FIG. 9 is a plan view of the apparatus of FIG. 8.

The structure and function of the remaining portions of mandrel 159 are substantially the same as that described with respect to mandrels 59 in respect to FIGS. 8, 9 and 10 so that description will not be repeated but may be considered to be incorporated by reference here.

It will be noted that, with respect to mandrels 159, center wall 116 of mandrel 59 has been eliminated as well as outer walls 115. The function of outer walls 115 is taken over by metal pins 160 in mandrel 159. It should be noted that the number and arrangement of metal pins 160 is not limited to that shown in FIGS. 17, 18, and 19 and one could readily use six or more such pins. If desired, metal pins 160 could be placed at the ends of the space previously occupied by center wall 116 and they would be accommodated by the bifurcated tongue 92 of pick-off element 201.

A modified pick-off element similar to pick-off element 201 is preferred for use with mandrels 159.

Figure 20:
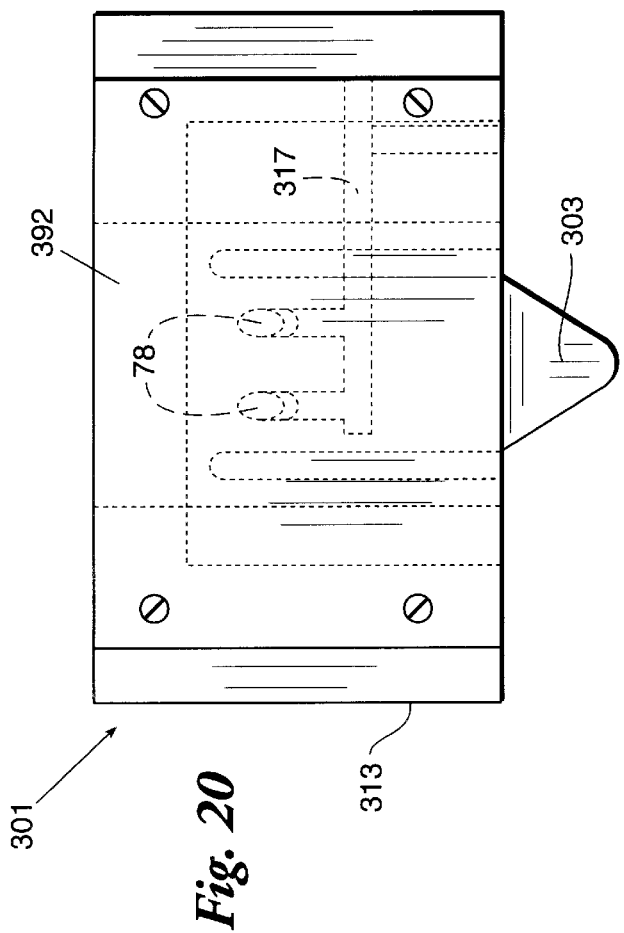
FIG. 20 is a top plan view of an alternative form of pick-off element.
Figure 21:
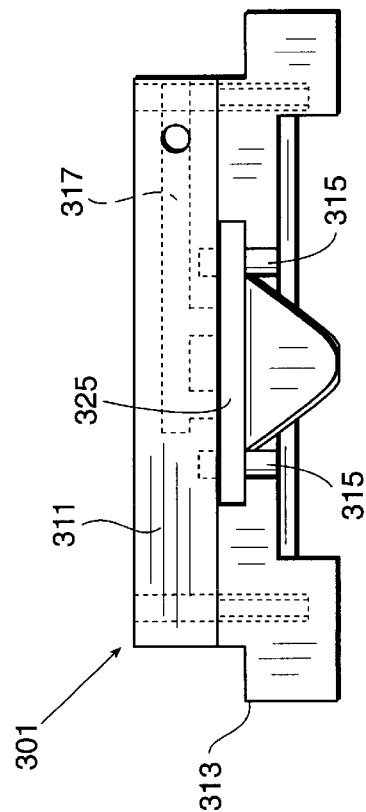
FIG. 21 is a front elevational view of the apparatus of FIG. 20.
Figure 22:
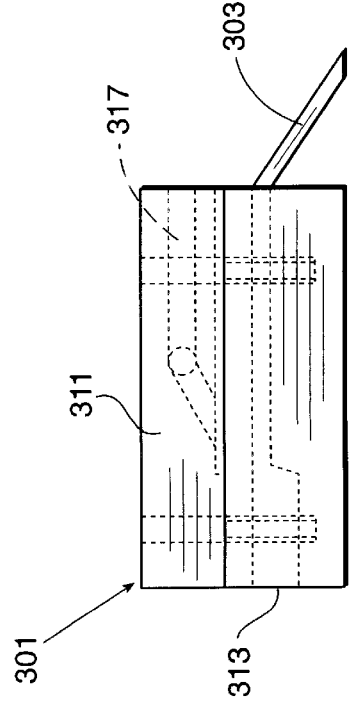
FIG. 22 is a side elevational view of the apparatus of FIG. 20.

Referring to FIGS. 20, 21, and 22, an alternative form of pick-off element 301 is shown which is particularly well adapted to cooperate with the alternative mandrel 159 shown in FIGS. 17, 18, and 19.

The pick-off element 301 shown in FIGS. 20, 21, and 22 is generally similar in function to pick-off element 201 shown in FIGS. 11–16, and as to such similarities it will not be described in detail.

As shown in FIG. 20, a tongue 392 is generally similar to tongue 92 shown in FIGS. 11–16 except that it is not bifurcated and the tongue extension 303 has a generally triangular shape adapted to insert in a mandrel underneath a coil wound on the mandrel. The forward tongue extension 303 is preferably bent down at an angle as shown in FIG. 22 to generally match the arcuate motion of a mandrel as it approaches the pick-off element 301. The top plate 311 is preferably formed of a hard plastic material and preferably a transparent material such as Lucite®. Top plate 311 has slots 315 positioned to accept entry of pins 160 on mandrel 159 as mandrel 159 moves under pick-off element 301. Since only narrow slots 315 are needed to accommodate the pins 160, a tunnel 325 is effectively formed in pick-off element 301 which is well adapted to confine and guide a coil 91 through the pick-off element 301. An air passage similar to air passage 218 shown in FIGS. 11–16 may be provided in the pick-off element 301 and, in general, the features of pick-off element 201 may be incorporated in pick-off element 301 and vice-versa. The base 313 of pick-off element 301 is generally similar to base 13 of pick-off element 201 except as described in relation to the slots 315 for entry of mandrel pins 160.

In addition to the modifications and variations in the invention which have been described, shown, or suggested above, it will be apparent to those skilled in the art that other variations and modifications to the invention may be effected and, accordingly, the scope of the invention is not to be considered limited to those described, shown, or suggested above.

What is claimed is:

1. In an individual dental floss segment packaging machine, apparatus for making a series of coils of dental floss strand material comprising:
   (A) a rotatable strand positioning element having an axis of rotation and a path of rotation;
   (B) means for guiding a continuous strand material to said rotatable strand positioning element;
   (C) a rotatable circular array of at least three mandrels positioned to permit a selected one of said mandrels to reside within said path of rotation;
   (D) means for sequentially positioning one of said mandrels within said path of rotation;
   (E) a motor driving said strand positioning element to wind turns of said strand material on said one of said mandrels;
   (F) a stepping motor for advancing said array to move said selected one of said mandrels and a predetermined number of turns of strand material forming a coil thereon from within said path of rotation and moving a second one of said mandrels inside said path of rotation;
   (G) means for supporting said coil located on said one of said mandrels and for retracting said one of said mandrels causing said coil to be removed therefrom while retaining a coil shape; and
   (H) a controller for repetitively advancing said array of mandrels and causing removal of said coil-shaped strands to produce a series of coils of strand material.

2. Apparatus as recited in claim 1 further including means for transporting each of said coils removed from one of said mandrels to a subsequent packaging stage position.

3. Apparatus as recited in claim 1 wherein said rotatable strand positioning element is mounted on a hollow shaft and said means for guiding a continuous strand material to said rotatable strand positioning element includes means for guiding said strand material through said hollow shaft of said rotatable strand positioning element.

4. Apparatus as recited in claim 1 wherein said means for supporting said coil located on said one of said mandrels includes a pick-off element insertable in an opening through said first mandrel below the coil formed on said mandrel in a manner to leave a coil formed by said turns on said pick-off element when said mandrel is retracted.

5. Apparatus as recited in claim 4 wherein each of said mandrels includes at least two rigid upright elements with a centrally located space between them forming an opening adapted to receive said pick-off element.

6. Apparatus as recited in claim 1 wherein said stepping motor for advancing said array to remove said selected one of said mandrels from within said path of rotation operates in a time equal to or less than the time for about one rotation of said rotatable strand positioning element.

7. Apparatus as recited in claim 1 further including means for causing a just removed coil to be captured between upper and lower elongated packaging film strips in near proximity having means for producing an air jet aimed to urge said just removed coil from a position above a retracted mandrel to within the space between said elongated packaging film strips in near proximity.

8. A process of making a series of coils of flexible strand material in an individual strand segment packaging process comprising the steps of:
   (A) supplying a strand material to a rotating strand positioning element having an axis of rotation from a supply roll substantially coaxial therewith;
   (B) placing a first mandrel having a transverse dimension of less than about three inches inside a path of rotation of said strand positioning element;
   (C) rotating said strand positioning element from three to twelve rotations to cause turns of said strand to be wound on said first mandrel;
   (D) removing said first mandrel and the strands wound thereon from said path of rotation by rotating a mounting element for said first mandrel and other mandrels by at least 10°;
   (E) placing a second mandrel inside said path of rotation;
   (F) causing said strand portion wound on said first mandrel to be removed therefrom while substantially retaining a coil shape imparted by said first mandrel by positioning a pick-off element in an opening through said first mandrel below the turns wound on said mandrel, and lowering said mandrel to leave said coil resting on said pick-off element;
   (G) repeating step (B) and subsequent steps substituting said second mandrel for said first mandrel and substituting a third mandrel for said second mandrel to produce a series of interconnected coils formed of said strand material supplied to said rotating strand positioning element.

9. A process as recited in claim 8 further including the step of transporting said strand portion removed from said first mandrel to a subsequent packaging stage position.

10. A process as recited in claim 8 wherein said step of removing said first mandrel from said path of rotation is carried out in a time less than one-half the time for one rotation of said rotating strand positioning element.

* * * * *

Disclaimer 5,934,046 - Dale Whittaker, Tulsa, Oklahoma. INDIVIDUAL DENTAL FLOSS PACKAGE FORMING METHOD AND APPARATUS. Patent dated August 10, 1999. Disclaimer filed October 1, 1999, by the inventor.

The term of patent shall not extend beyond the expiration date of Pat. No. 5,765,343.
*(Official Gazette, December 28, 1999)*